United States Patent [19]

Schwabe et al.

[11] Patent Number: 5,093,165
[45] Date of Patent: Mar. 3, 1992

[54] USE OF FILMS COMPOSED OF PLASTICS HAVING POLAR MOLECULAR GROUPS AS PRIMARY PACKAGING FOR β-LACTAM ANTIBIOTICS, AND PLASTIC BAGS

[75] Inventors: Karl-Detlev Schwabe, Frankfurt am Main; Wolfgang Pohler, Hofheim am Taunus; Elisabeth Toth, Rüsselsheim, all of Fed. Rep. of Germany

[73] Assignee: Hoechst Aktiengesellschaft, Frankfurt am Main, Fed. Rep. of Germany

[21] Appl. No.: 434,449

[22] Filed: Nov. 13, 1989

Related U.S. Application Data

[63] Continuation of Ser. No. 234,122, Aug. 17, 1988, abandoned.

[30] Foreign Application Priority Data

Aug. 19, 1987 [DE] Fed. Rep. of Germany ....... 3727627

[51] Int. Cl.$^5$ .............................................. B65D 85/00
[52] U.S. Cl. .................................. 428/35.5; 206/524.1
[58] Field of Search ............................ 428/35.5, 35.1; 206/524.1

[56] References Cited

U.S. PATENT DOCUMENTS 4,042,562  8/1977  Hafer ...................... 524/97
4,561,110 12/1985  Herbert .................. 604/408

FOREIGN PATENT DOCUMENTS 0216639  4/1987  European Pat. Off. .
2907951  9/1980  Fed. Rep. of Germany .
3318875 11/1984  Fed. Rep. of Germany .
WO86/02042  4/1986  PCT Int'l Appl. .

OTHER PUBLICATIONS

Modern Packaging Encyclopedia, vol. 39, No. 4A, Dec. 1965, pp. 139, 142–143, 154–157 and 180–181.
"The Packaging Reference Issue", 1986, pp. 52–53 and 62–63.

Primary Examiner—James J. Seidleck
Attorney, Agent, or Firm—Finnegan, Henderson, Farabow, Garrett and Dunner

[57] ABSTRACT

The use of films composed of plastics having polar molecular groups as primary packaging for solid β-lactam antibiotics is described. Plastic bags composed of the said plastics form the primary packaging.

3 Claims, No Drawings

USE OF FILMS COMPOSED OF PLASTICS HAVING POLAR MOLECULAR GROUPS AS PRIMARY PACKAGING FOR β-LACTAM ANTIBIOTICS, AND PLASTIC BAGS

This is a continuation of application Ser. No. 07/234,122, filed Aug. 17, 1988 now abandoned.

DESCRIPTION

Sterile cephalosporin derivatives which are to be handled aseptically and used for the preparation of injectable compositions, such as, for example, cefotaxime, cefodizime, cefpirome, as well as 1-[[(6R, 7R)-7-[2-(2-amino-4-thiazolyl)glyoxylamido]-2-carboxy-8-oxo-5-thia-1-azabicyclo[4.2.0]oct-2-en-3-yl]-methyl]-5,6,7,8-tetrahydroquinoliniumhydroxide, inner salt, $7^2$-(Z)-(O-methyloxime) (also called HOE 111), as well as the physiologically tolerated salts thereof, where appropriate mixed with pH-regulating substances, are packaged in sterile polyethylene plastic bags as primary packaging. The flexible bags are easy to handle and show no particle abrasion as occurs, in particular, at the sealing elements in the case of inflexible primary packaging, for example composed of stainless steel or glass.

It is a disadvantage that, on storage, polyethylene, and in the same way also polypropylene, plastic bags cause the packaged substances to give cloudy solutions, even when both bag and substance to be packaged were sterile and packaging took place under aseptic conditions. However, substances used to prepare injectable solutions must give clear solutions.

Attempts to replace the known primary packaging by composite films composed of polyamide/low-density polyethylene, composite films composed of polyester/low-density polyethylene or composite films composed of polyester/aluminum/polyethylene, as are mainly used for packaging foodstuffs, have not shown the desired result; the solutions were found to be cloudy to the same extent. This represents no improvement whatever from the polyethylene and polypropylene bags used. These observations mean that those skilled in the art would have expected bags composed of plastics having polar molecular groups also to be unsuitable as primary packaging for β-lactam antibiotics, because they are more chemically reactive than polyethylene and polypropylene.

It has now been found, surprisingly, that when plastic bags composed of plastics having polar molecular groups, such as, for example, cellulose film, polyamide, polyester, polyurethane or cellulose acetate, are used no cloudiness is caused in solutions of cephalosporin derivatives.

Hence the invention relates to the use of films composed of plastics having polar molecular groups as primary packaging for solid β-lactam antibiotics, and to plastic bags composed of films of plastics having polar molecular groups as primary packaging for solid β-lactam antibiotics.

Particularly suitable plastics having polar molecular groups are cellophane film (for example (®) Cellophan), cellulose acetate, polyamide (for example (®) Pla-Steril), polyesters and polyurethanes. Cellulose film, polyamide and polyesters are preferably used.

Plastic bags composed of the said films can, in contrast to plastic bags composed of polyethylene, be sterilized in an autoclave. Gas-sterilization, for example with formaldehyde or ethylene oxide, is possible but can be avoided because of the heat-resistance, which has the advantage that it is no longer possible for residues of the sterilizing gas to occur in the primary packaging.

The films can be produced under aseptic conditions or clean-room conditions and must not have any adherent dust particles—even sterile ones—i.e. contamination of the pharmaceutical must be ruled out a priori.

The bags are obtained, for example, by folding or welding the film. The bags for the primary packaging are sealed with wire ties. The thickness of the film depends, of course, on the strength of the film and on the amount of active substance to be introduced into the bag. The bags have adequate mechanical stability, no abrasion has been observed.

Suitable β-lactam antibiotics are principally cephalosporins, especially cefotaxime, cefodizime, cefpirome and HOE 111, as well as the physiologically tolerated salts thereof, where appropriate mixed with pH-regulating compounds. Examples of suitable pH-regulating compounds are sodium carbonate, trisodium phosphate and basic amino acids.

The examples which follow show that when films composed of the said plastics are used, the pharmaceuticals are found to give the clear solutions prescribed, even under different types of stress, whereas a cloudiness of the solutions was perceptible with the naked eye when polyethylene film was used.

Example I: Cefodizime di-Na salt 0.5 g dosage packaged in bags (length 5 cm, width 4 cm)

|  | Polyethylene film | Polyamide film | cellophane film | Polyester film |
| --- | --- | --- | --- | --- |
| 1 h vibration | cloudy solution | clear solution | clear solution | clear solution |
| 1 h vibration then storage at +40° C. for 7 days | cloudy solution | clear solution | clear solution | clear solution |
| 1 h vibration then storage at room temperature for 7 days | cloudy solution | clear solution | clear solution | clear solution |
| 1 h vibration then storage at +5° C. for 7 days | cloudy solution | clear solution | clear solution | clear solution |
| Storage at +40° C. for 7 days | cloudy solution | clear solution | clear solution | clear solution |
| Storage at room temperature for 7 days | cloudy solution | clear solution | clear solution | clear solution |
| Storage at +5° C. for 7 days | cloudy solution | clear solution | clear solution | clear solution |

Example II: Cefotaxime Na salt 0.5 g dosage packaged in bags (length 5 cm, width 4 cm)

|  | Polyethylene film | Polyamide film | cellophane film | Polyester film |
|---|---|---|---|---|
| 1 h vibration | cloudy solution | clear solution | clear solution | clear solution |
| 1 h vibration then storage at +40° C. for 7 days | cloudy solution | clear solution | clear solution | clear solution |
| 1 h vibration then storage at room temperature for 7 days | cloudy solution | clear solution | clear solution | clear solution |
| 1 h vibration then storage at +5° C. for 7 days | cloudy solution | clear solution | clear solution | clear solution |
| Storage at +40° C. for 7 days | cloudy solution | clear solution | clear solution | clear solution |
| Storage at room temperature for 7 days | cloudy solution | clear solution | clear solution | clear solution |
| Storage at +5° C. for 7 days | cloudy solution | clear solution | clear solution | clear solution |

Example III: Cefpirome sulfate/sodium carbonate mixture with 5 cm$^2$ bag film per g

|  | Polyethylene film | Polyamide film | Cellophane film | Polyester film | Without film for comparison |
|---|---|---|---|---|---|
| Rolling for 7 days | cloudy solution | clear solution | clear solution | clear solution | clear solution |
| Storage at room temperature for 7 days after mixing | cloudy solution | clear solution | clear solution | clear solution | clear solution |
| Storage at +40° C. for 7 days after mixing | cloudy solution | clear solution | clear solution | clear solution | clear solution |

We claim:

1. A plastic bag for packaging material, comprising a single component plastic film having polar molecular groups, selected from the group consisting of cellophane, cellulose acetate, polyamide, polyester and polyurethane, wherein the material packaged by said bag is a cephalosporin derivative.

2. The plastic bag as claimed in claim 1, wherein said cephalosporin derivative is selected from the group consisting of cefotaxime, cefodizime, cefpirome and HOE 111 or their physiologically tolerated salts.

3. The plastic bag as claimed in claim 1, wherein the material packaged by said bag further contains a pH-regulating compound.

* * * * *